United States Patent [19]

Gay

[11] Patent Number: 4,470,699
[45] Date of Patent: Sep. 11, 1984

[54] MICRO-COLUMN PLASMA EMISSION LIQUID CHROMATOGRAPH

[75] Inventor: Don D. Gay, Aiken, S.C.

[73] Assignee: The United States of America as represented by the United States Department of Energy, Washington, D.C.

[21] Appl. No.: 407,538

[22] Filed: Aug. 12, 1982

[51] Int. Cl.³ .............................................. G01N 21/73
[52] U.S. Cl. .................................................... 356/316
[58] Field of Search ............... 356/311, 313, 314, 315, 356/316, 417

[56] References Cited

U.S. PATENT DOCUMENTS

| | | | |
|---|---|---|---|
| 3,055,262 | 9/1962 | Ducati et al. | 356/316 |
| 3,242,798 | 3/1966 | Yamamoto | 356/316 |
| 3,610,759 | 10/1971 | Wood et al. | 356/316 |
| 3,612,686 | 10/1971 | Braman et al. | 356/316 |
| 3,802,782 | 4/1974 | Natelson | 356/316 |
| 3,958,883 | 5/1976 | Turner | 356/316 |
| 4,225,235 | 9/1980 | Anderson et al. | 356/316 |
| 4,256,404 | 3/1981 | Walker | 356/316 |
| 4,351,643 | 9/1982 | Govindaraju | 356/316 |

OTHER PUBLICATIONS

Ishii et al., *Journal of Chromatography*, vol. 144, 1977, pp. 157-168.
Ishii et al., *Journal of Chromatographic Science*, vol. 18, Sep. 1980, pp. 462-472.
McGuffin et al., *Analytical Chemistry*, vol. 53, No. 7, Jun. 1981, pp. 946-951.
Lloyd et al., *Analytical Chemistry*, vol. 50, No. 14, Dec. 1978, pp. 2025-2029.
Schäfer et al., *Journal of Chromatography*, vol. 206, Feb. 1981, pp. 245-252.
Novotny, *Journal of Chromatographic Science*, vol. 18, Sep. 1980, pp. 473-478.
Takeuchi et al., *Journal of Chromatography*, vol. 213, Aug. 1981, pp. 25-32.
Reese et al., *Journal of Chromatographic Science*, vol. 18, Sep. 1980, pp. 479-486.
Krien et al., *Journal of Chromatography*, vol. 251, 1982, pp. 129-139.
Dedieu et al., *Journal of Chromatography*, vol. 251, 1982, pp. 202-213.

*Primary Examiner*—F. L. Evans
*Attorney, Agent, or Firm*—Allen F. Westerdahl; Michael F. Esposito

[57] ABSTRACT

In a direct current plasma emission spectrometer for use in combination with a micro-column liquid chromatograph, an improved plasma source unit. The plasma source unit includes a quartz capillary tube having an inlet means, outlet off gas means and a pair of spaced electrodes defining a plasma region in the tube. The inlet means is connected to and adapted to receive eluant of the liquid chromatograph along with a stream of plasma-forming gas. There is an opening through the wall of the capillary tube penetrating into the plasma region. A soft glass capillary light pipe is disposed at the opening, is connected to the spectrometer, and is adapted to transmit light passing from the plasma region to the spectrometer. There is also a source of electromotive force connected to the electrodes sufficient to initiate and sustain a plasma in the plasma region of the tube.

6 Claims, 1 Drawing Figure

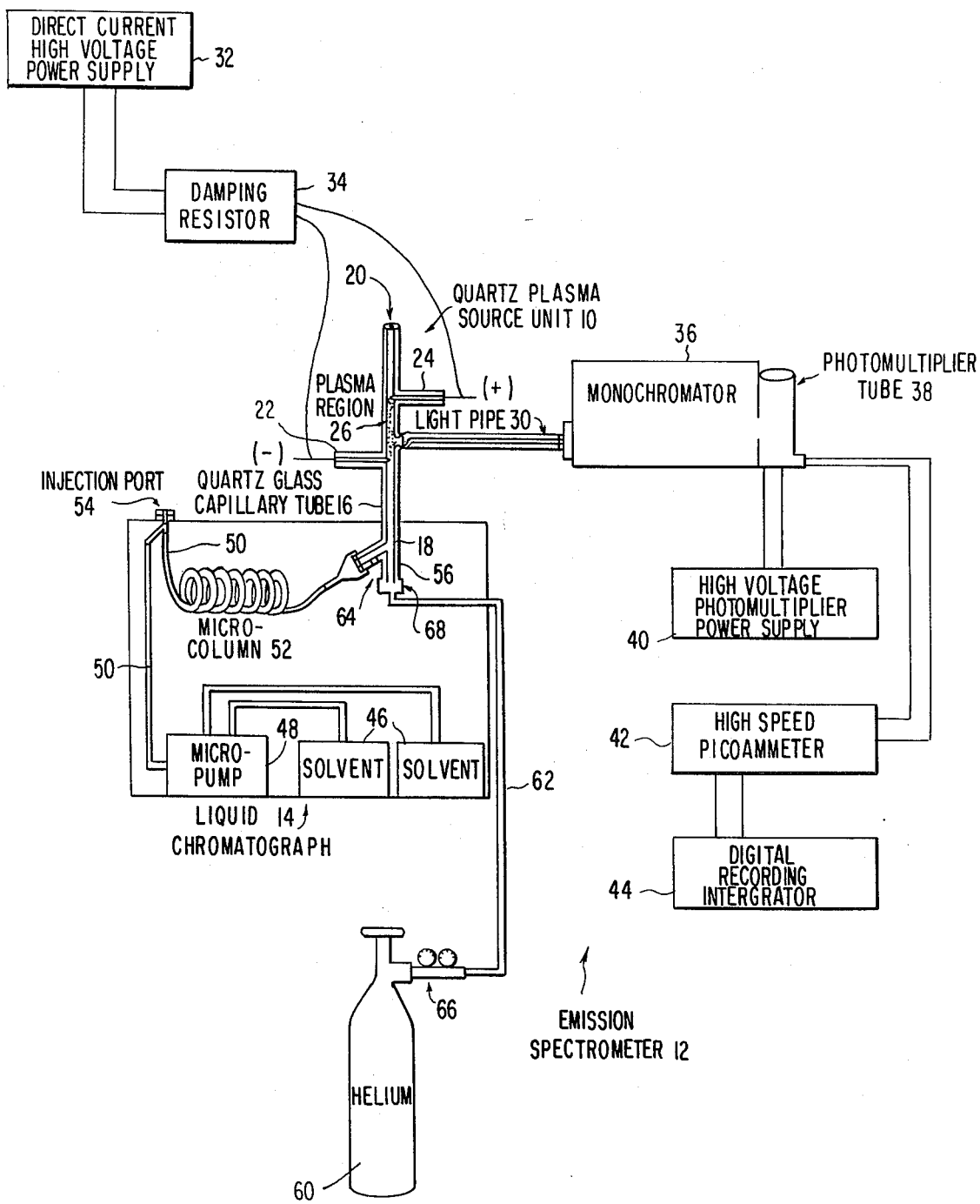

MICRO-COLUMN PLASMA EMISSION LIQUID CHROMATOGRAPH

BACKGROUND OF THE INVENTION

1. Field of the Invention and Contract Statement

The invention relates to direct current plasma emission spectrometers for use in combination with a micro-column liquid chromatograph. The United States Government has rights in this invention pursuant to Contract No. DE-AC09-76SR00001 between the U.S. Department of Energy and E. I. DuPont de Nemours & Co.

2. Discussion of Background and Prior Art

Chromatography is a physical method of separation, in which the components to be separated are distributed between two phases, one of these phases constituting a stationary bed of large surface area, the other being a fluid that percolates through or along the stationary bed. The stationary phase can be either a solid or a liquid, and the moving phase may be either a liquid or a gas. All of the known types of chromatography broadly fall into four categories, namely liquid-solid, gas-solid, liquid-liquid, and gas-liquid. In all of the known chromatographic techniques, the solutes to be separated migrate along a column (or, as in paper or thin layer chromatography, the physical equivalent of a column), and of course the basis of the separation lies in different rates of migrations for the different solutes. The rate of migration of a solute is the result of two factors, one tending to move the solute and the other to retard it.

Liquid chromatography (LC) is a rapidly expanding analytical technique for the separation of chemical compounds which have low or non-existent vapor pressures and are water soluble. The conventional detection systems for liquid chromatography are based on the refractive indices, absorption, fluorescent or electrochemical properties of the compounds in question. Such detectors do not offer selectivity or sensitivity of the magnitude provided by detectors for gas chromatography.

Micro-column liquid chromatographic systems are currently in the infancy of the state-of-the-art development of liquid chromatography. Three basic nomenclatures define micro-column liquid chromatography: (1) open tubular liquid chromatography; (2) microbore liquid chromatography; and (3) capillary liquid chromatography. Inherent with all three designs are (a) extremely high theoretical plate separations, (b) high mass sensitivities and (c) extremely low solvent flow rates (1 to 5 $\mu$l/min as compared to 40 to 100 ml/min. for conventional liquid chromatographs).

In plasma emission spectroscopy, injection of liquid samples, and of effluent fluids from a chromatographic column, into the plasma space of a source are known. One of the problems before has always been how to get rid of the excess solvent before it hits the plasma region. Conventional flow rates do not allow an excited plasma state to remain in effect. The use of micro-columns in liquid chromatography provides a reduction in solvent flow rate.

SUMMARY OF THE INVENTION

An object of the invention is to provide an improved detection system for liquid chromatography which has much better selectivity and sensitivity than the prior art detectors. Other objects and advantages of the invention are set out herein or are obvious herefrom to one ordinarily skilled in the art.

The objects and advantages of this invention are achieved by the improved detection system of the invention.

To achieve the foregoing and other objects and in accordance with the purpose of the invention, as embodied and broadly described herein the invention, a direct current plasma emissiom spectrometer for use in combindation with a micro-column liquid chromatograph, provides an improved plasma source unit. The plasma source unit includes a quartz capillary tube having an inlet means, outlet off gas means and a pair of spaced electrodes defining a plasma region in the tube. The inlet means is connected to and adapted to receive eluant of the liquid chromatograph along with a stream of plasma-forming gas. There is an opening through the wall of the capillary tube penetrating into the plasma region. A soft glass capillary light pipe is disposed at the opening, is connected to the spectrometer, and is adapted to transmit light passing from the plasma region to the spectrometer. There is also a source of electromotive force connected to the electrodes sufficient to initiate and sustain a plasma in the plasma region of the tube. The prior art, for example, does not show the use of the opening penetrating into the plasma region in conjunction with a light tube.

The detection system for liquid chromatography of the invention gives elemental selectivity as well as has 100 to 1000 times more sensitivity than current liquid chromatography detectors. The invention detector is an atmospheric-pressure direct-current helium-plasma emission spectrometer. When coupled to a micro-column liquid chromatograph, sensitivity and selectivity can be significantly gained for liquid chromatography. The invention detector incorporates a new approach to liquid chromatography that is based upon the use of micro-columns for increased power in chemical separations and plasma emission spectroscopy for increased detectability of eluted chemical compounds. The invention involves the coupling of a micro-column with a plasma emission spectrometer.

Preferably the plasma-forming gas is helium. Also, preferably the opening on the side of the capillary tube is between about 1 and 2 mm diameter.

The capillary light pipe preferably has highly-polished internal walls. Further, preferably the capillary light pipe has a diameter between about 2 mm and 3 mm, and is disposed to maintain a gap of about 1 to 2 mm between the light pipe and the opening in the capillary tube.

Some of the advantages of micro-column plasma emission liquid chromatography using the invention detector over conventional and commercially available liquid chromatography are:

(1) Increased sensitivity (100 to 1000 times greater sensitivity). Atomic emission (which the invention uses) is far superior in sensitivity to atomic absorption, fluorescence, electrochemical or refractive indices measurements currently employed as detection mechanisms for liquid chromatography. The increase in sensitivity is 100 to 1000 greater with emission spectroscopy (using invention detector).

(2) Increased selectivity. The plasma emission detector is element specific and selective. Each element emits characteristic wavelengths of light. This detector capitalizes upon that by being continuously tunable to various wavelengths of interest. No other liquid chromatographic detector offers this feature.

(3) Increased stablity. Problems with etching, solvent polymerization and carbon formation on the walls of the plasma source unit encountered by other detectors are minimized or eliminated with the invention detector. The sensitivity of other plasma source units is deleteriously affected by wall etching due to high temperatures, solvent polymerization and carbon formation on the walls, but the invention detector is not affected by these problems.

(4) Very high signal to noise ratio. Such is accomplished by the invention by selectively looking at the most reactive region of the plasma rather than the entire plasma. Such feature is unique to the invention detector. The invention detector looks at a fraction of the total plasma rather than the entire plasma as in other plasma detectors. The fraction utilized is the region giving the greatest elemental emission signal. Therefore, this signal response is not diluted or averaged over the entire plasma and a greater response is obtained.

(5) Increased power in separating similar chemical species. The micro-column approach offers a greater number of theoretical plates for separation efficiency and a higher mass sensitivity than conventional liquid chromatographic columns. The power of a liquid chromatographic column in separating compounds is based upon the number of theoretical plates available in the column. The greater the number of theoretical plates, the more power is available to distinctly separate chemically-similar compounds. Conventional liquid chromatography does not have the power to separate these as easily as the invention instrument. Micro-columns offer substantially more theoretical plates for separation power.

(6) Very low solvent usage. Solvent flow rates for micro-column liquid chromatography are 1 to 10 $\mu$l/min., while conventional flow rates are 40 to 100 ml/min. Ultra-pure solvents for liquid chromatography currently cost about $15 to $30 per gallon. A reduction of $10^4$ to $10^5$ in the solvent usage is obtained with micro-columns.

Due to the sensitivity, selectivity, and separation power achieved by the invention instrument, significant advancement in clinical and diagnostic tests can be obtained in the human health professions as well as in other areas, particularly biochemistry, pharmacology, toxicology, physiology, nutrition, genetic manipulations and the like. Almost every area of science can benefit from the use of the invention instrument because more than 80 percent of all known compounds are water soluble and are amenable to liquid chromatographic techniques.

Reference will now be made in detail to the present preferred embodiment of the invention, an example of which is illustrated in the accompanying drawing.

A BRIEF DESCRIPTION OF THE INVENTION

The accompanying drawing, which is incorporated in and forms a part of the specification, illustrates the invention and, together with the description serves to explain the principles of the invention. In the drawing:

The FIGURE is a schematic diagram of the system of the invention.

DETAILED DESCRIPTION OF THE INVENTION

All parts, percentages ratios and proportions are on a weight basis unless otherwise stated herein or obvious herefrom to one ordinarily skilled in the art.

Referring to the FIGURE, a preferred embodiment is disclosed wherein plasma source unit 10 is coupled with emission spectrometer 12 and micro-column liquid chromatograph 14. Plasma source unit 10 includes a quartz glass capillary tube 16 having inlet 18 for receiving chromatograph eluant along with a stream of plasma-forming gas from 68, and outlet off-gas means 20. Electrodes 22 and 24 define plasma region 26. Opening 28 in the wall of capillary tube 16 penetrates into plasma region 26. One end of soft glass capillary light pipe 30 is disposed at opening 28 and the other end thereof is connected to spectrometer 12 to transmit light to it from plasma region 26. Basically, the invention is a new analytical approach to liquid chromatography combining micro-column liquid chromatograph 14 with direct current plasma emission spectrometric detector 10, 12.

Direct current high voltage power source 32 is electrically connected to electrodes 22 and 24 with intermediate damping resistor 34. The noted end of light pipe 30 is connected to monochromator 36. Emission spectrometer 12 includes monochromator 36, photomultiplier tube 38, high-voltage photomultiplier power source 40, high-speed picoammeter 42, which is electrically connected to photomultiplier tube 38, and digital recording integrator 44, which is electrically connected to picoammeter 42.

Micro-column liquid chromatograph 14 includes solvent containers 46 connected to micro-pump 48, which in turn is connected by line 50 to coiled, micro-column 52. Injection port 54 is situated in line 50 between micro-pump 48 and micro-column 52. Inlet 18 of capillary tube 16 has a lower end 56 and side arm 58. One end of micro-column 52 is connected to side passageway 58. Chromatograph solvent is forced into line 50 by means of micro-pump 48 and is transported to inlet 18 of capillary tube 16 via micro-column 52 and side arm 58. Sample is injected into injection port 54 and is transported, along with solvent from line 50, to inlet 18 of capillary tube 16 via micro-column 52 and side arm 58. Ultra high pure (U.H.P.) helium from pressurized tank 60 flows into lower end 56 of inlet 18 via line 62 at 68 and is regulated by valves 66.

The heart of the direct current plasma emission spectrometric detector of the invention is plasma source unit 10. It is quartz capillary tube 16 through which helium gas is forced between two electrodes 22 and 24. The plasma, or region of excitation (26), occurs between electrodes 22 and 24. Conventional plasma source units have a contained region for the plasma. The emitted light passes through the quartz capillary walls, through a quartz lens (or reflected by highly polished mirrors) into a variable wavelength monochromator entrance slit or through special filters. The selected wavelengths impinge upon a photomultiplier tube which changes light energy into electrical impulses.

Invention plasma source unit 10 has a specific region (26) for plasma excitation. However, a very small diameter hole 28, termed the "viewing port", is drilled through one wall of quartz capillary tube 16 near cathode 22. Instead of a conventional quartz lens or mirror, the invention uses a piece of soft glass capillary tubing 30 having highly polished internal walls to focus the light emitted from the plasma into the entrance slit of variable-wavelength monochromator 36. Soft glass capillary tube 30 is termed a "light pipe." The emitted light from the highly energetic helium plasma (26) is transmitted directly into monochromator 36.

One serious problem with conventional contained quartz plasma units is that signal deterioration occurs almost immediately with the use of a new quartz capillary tube. Etching of the quartz walls occurs rapidly because the temperature of the plasma is 3000° to 5000° C. Such etching allows less and less light to be transmitted through the walls into the monochromator and photomultiplier tube. Also, solvent polymerization and carbon buildup on the internal walls of the quartz capillary tube necessitate frequent cleanings to let the emission light pass through. With the use of quartz lenses or mirrors as focusing devices, almost all (if not all) of the plasma region is focused onto the entrance slit of the monochromator. Various studies have shown that all regions of the plasma do not cause equal light emissions from elements under investigation.

Invention plasma source unit 10 effectively reduces or eliminates all of the afore-mentioned problems associated with conventional plasma source units and focusing devices. Because "viewing port" 28 directly into the plasma (26) is used, etching of the quartz walls does not make any difference on the signal. The life span and functionality of quartz plasma source unit 10 is 10 to 50 times greater (at least) than conventional source units. Solvent polymerization and carbon formation do occur in the invention unit, but signal degradation does not occur. Introduction of small quantities of oxygen into the helium flow reduces this carbon buildup. Lastly, by having "viewing port" 28 near cathode 22, which is the most sensitive region of plasma 26 for most elements, and using glass "light pipe" 30 to transmit only the light from port 28 into monochromator 36, the highest signal to noise ratio can be obtained and maintained.

Helium is preferred over argon as the gas for the plasma, because it produces a higher temperature as a plasma and is more energetic than argon. Most applications using helium as a plasma source require the helium to be maintained under reduced pressure in order for a plasma to be initiated. With the invention system, a functional helium plasma is initiated and maintained at standard atmospheric pressure. The plasma is automatically initiated when the current and voltage applied to electrodes 22 and 24 reach a certain level. In order to make the invention system fully automatic in regard to plasma initiation, large damping resistor 34 is built into the electric lines to electrodes 22 and 24. The required settings for initiation can be maintained on the direct current power supply 32, so that if the plasma is extinguished by the passage of a large volume of solvent, the plasma will re-initiate itself once the solvent has passed.

To couple micro-column 52 to plasma source unit 10, auxiliary sidearm 58 is attached to the central axis of capillary tube 16 just below plasma region 26. Sidearm 58 receives the eluant from micro-column 52 through nebulizer 64. The attachment region of sidearm 58 is very narrow and serves as nebulizer or atomizer 64. This is the preferred version of the nebulizer.

Alternatively, the nebulizer of U.S. Pat. No. 3,958,883 can be used. The pertinent parts of U.S. Pat. No. 3,958,883 are incorporated herein by reference.

Another method for attaining the atomization required is given in Krien et al., "Application of Microbore Columns to Liquid Chromatography-Mass Spectrometry", Journal of Chromatography 251(2), 129–139, (1982), the pertinent parts which are incorporated herein by reference. See the diagram on bottom of page 131 of Krien et al. The same thing they have done with the 0.5 $\mu$m porosity filter in the micro-column end, covered by a porous diaphram works very well in the system shown in the FIGURE by inserting the covered and filtered micro-column end into sidearm 58 up to the junction with the central axis (16). The eluant from the micro-column having the porosity filter and diaphragm emerges as a fine spray into the helium gas stream and is further atomized in it as it passes to the electrode plasma region 26. Heating the region between sidearm 58 and cathode 22 facilitates a better combination of eluant and helium hitting the plasma. Alternatively, the scheme of Dedieu et al., "Application of a Combined Liquid-Chromatography", 251(2), 202–213, (1982), the pertinent parts which are incorporated herein by reference, can be used. Dedieu et al. teaches a high-speed direct liquid introduction device as diagrammed at the bottom of page 207 therein. The end of the micro-column (termed "LC probe" in the diagram) can be fitted with the small "heated chambers" configuration as depicted and the entire structure inserted into the sidearm 58 up to the junction with the central axis (16). Also, the scheme of Schafer et al., "Direct Coupling of a Micro-High Performance Liquid Chromatograph and a Mass Spectrometer", Jour. Chromatography 206(2), 245–252 (1981), the pertinent parts which are incorporated herein by reference, can be used. In Schafer et al. the effluent from the micro-column (termed capillary in Schafer et al.) goes directly into the helium gas stream without a special nebulizer. This is similar to the preferred version of the nebulizer set out above.

The atomized eluant from the nebulizer 64 passes from sidewarm 58 into the helium gas stream in the central region of capillary tube 16. This mixture of helium and atomized eluant then passes into plasma region 26 between electrodes 22 and 24.

Micro-column 52 separates the chemical compounds on the basis of chemical properties. The detection of the compounds on the basis of the emission spectrum of the element selected for monitoring is determined via variable wavelength monochromator 36.

A helium plasma is maintained after initiation with at least a 95 percent concentration of helium in plasma region 26. With less than 95 percent helium, the plasma is extinguished. The helium carrier gas flow rate normally used is 50 to 200 ml/min. The microcolumn (52) flow rate of the solvent is 1 to 10 $\mu$l/min. With a 22-fold increase in volume when the liquid solvent is converted to a gas, the concentration of helium in plasma region 26 with a 50 ml/min. helium flow rate and 1 $\mu$l/min. effluent flow from micro-column 52 is 99.9 percent. Increasing the effluent flow to 10 $\mu$l/min. gives a helium concentration in plasma region 26 of 99 percent; the helium plasma is not extinguished.

Any suitable or conventional solvent, such as, acetonitrile-water, methanol-water, methanol, n-hexane-methanol-dichloromethane, acetonitrile-hexane, isopropanol-hexane, and n-hexane-methanol, can be used.

Because of the unique detector system of the invention, the invention instrument has wide applications in determining heavy metals in diverse matrices. In addition, by selectively tuning monochromator 36 to ubiquitous elements, e.g., C, S, N and P, the invention instrument becomes a universal detection system for determinations involving complex organic molecules (peptides, proteins, lipids, fatty acids and polysaccharides), pesticides, herbicides, carcinogens, mutagens, amines, amides and other chemical compounds.

By way of summary, the invention involves a microcolumn liquid chromatograph having a low solvent flow rate combined with a D.C. plasma emission spectrometer having a unique detector design. The plasma source unit uses a "light pipe" of soft glass capillary tubing disposed in a small viewing port opening into the plasma region of the quartz plasma tube. This light pipe takes the place of conventional quartz lens or mirrors used in prior art plasma emission spectrometers. The apparatus of the invention has wide use in the analytical determination of heavy metals in various matrices.

The foregoing description of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. In a direct current plasma emission spectrometer for use in combination with a micro-column liquid chromatograph, an improved plasma source unit which comprises:

(A) a quartz capillary tube having an inlet means, outlet off gas means, and a pair of spaced electrodes defining a plasma region in said tube:
      (i) said inlet means being connected to and adapted to receive eluant of said liquid chromatograph along with a stream of plasma-forming gas;
      (ii) an opening through the wall of said capillary tube penetrating into said plasma region; and
      (iii) a soft glass capillary light pipe being disposed at said opening, being connected to said spectrometer, and adapted to transmit light passing from said plasma region to said spectrometer; and
   (B) a source of electromotive force connected to said electrodes sufficient to initiate and sustain a plasma in said plasma region of said tube.

2. The improvement as claimed in claim 1 wherein said plasma-forming gas is helium.

3. The improvement as claimed in claim 1 wherein said electrodes include an anode connection and a cathode connection and said opening is located near said cathode connection of said electromotive force source to said capillary tube.

4. The improvement as claimed in claim 1 wherein said opening is between about 1 and 2 mm diameter.

5. The improvement as claimed in claim 1 wherein said capillary light pipe has highly-polished internal walls.

6. The improvement as claimed in claim 1 wherein said capillary light pipe has a diameter of between about 2 mm and 3 mm, and is disposed to maintain a gap of about 1 to 2 mm between said light pipe and said opening in said capillary tube.

* * * * *